(12) United States Patent
Gysling et al.

(10) Patent No.: US 7,275,421 B2
(45) Date of Patent: *Oct. 2, 2007

(54) APPARATUS AND METHOD FOR MEASURING PARAMETERS OF A MIXTURE HAVING SOLID PARTICLES SUSPENDED IN A FLUID FLOWING IN A PIPE

(75) Inventors: Daniel L. Gysling, Glastonbury, CT (US); Douglas H. Loose, Southington, CT (US)

(73) Assignee: CiDRA Corporation, Wallingford, CT (US)

( * ) Notice: Subject to any disclaimer, the term of this patent is extended or adjusted under 35 U.S.C. 154(b) by 45 days.

This patent is subject to a terminal disclaimer.

(21) Appl. No.: 10/512,401

(22) PCT Filed: Apr. 24, 2003

(86) PCT No.: PCT/US03/12956

§ 371 (c)(1),
(2), (4) Date: Oct. 22, 2004

(87) PCT Pub. No.: WO03/091671

PCT Pub. Date: Nov. 6, 2003

(65) Prior Publication Data

US 2005/0171710 A1    Aug. 4, 2005

Related U.S. Application Data

(63) Continuation-in-part of application No. 10/376,427, filed on Feb. 26, 2003, now Pat. No. 7,032,432, and a continuation-in-part of application No. 10/349,716, filed on Jan. 23, 2003.

(60) Provisional application No. 60/426,724, filed on Nov. 15, 2002, provisional application No. 60/425,436, filed on Nov. 12, 2002, provisional application No. 60/375,847, filed on Apr. 24, 2002, provisional application No. 60/359,785, filed on Feb. 26, 2002, provisional application No. 60/351,232, filed on Jan. 23, 2002.

(51) Int. Cl.
G01N 29/024    (2006.01)
G01N 29/14    (2006.01)

(52) U.S. Cl. .................. 73/61.79; 73/61.41; 73/61.49; 73/597; 73/643

(58) Field of Classification Search ............... 73/61.41, 73/61.47, 61.49, 61.79, 597, 643, 653, 656, 73/657; 702/54

See application file for complete search history.

(56) References Cited

U.S. PATENT DOCUMENTS 3,751,979 A    8/1973    Ims
(Continued)

FOREIGN PATENT DOCUMENTS

DE    4306119    3/1999
(Continued)

OTHER PUBLICATIONS

"Noise and Vibration Control Engineering Principles and Applications", Leo L. Beranek and Istvan L. Ver, A. Wiley Interscience Publication, pp. 537-541, Aug. 1992.
(Continued)

Primary Examiner—Daniel S. Larkin
(74) Attorney, Agent, or Firm—Michael Grillo

(57) ABSTRACT

An apparatus 10 and method is provided that includes a spatial array of unsteady pressure sensors 15-18 placed at predetermined axial locations $x_1$-$x_N$ disposed axially along a pipe 14 for measuring at least one parameter of a solid particle/fluid mixture 12 flowing in the pipe 14. The pressure sensors 15-18 provide acoustic pressure signals $P_1(t)$-$P_N(t)$ to a signal processing unit 30 which determines the speed of sound $a_{mix}(\omega)$ of the particle/fluid mixture 12 in the pipe 14 using acoustic spatial array signal processing techniques. The primary parameters to be measured include fluid/particle concentration, fluid/particle mixture volumetric flow, and particle size. Frequency based sound speed is determined utilizing a dispersion model to determine the parameters of interest. the calculating the at least one parameter uses an acoustic pressure to calculate.

53 Claims, 9 Drawing Sheets

U.S. PATENT DOCUMENTS

| | | | |
|---|---|---|---|
| 3,781,895 A | 12/1973 | Monser | |
| 3,851,521 A | 12/1974 | Ottenstein | |
| 3,885,432 A | 5/1975 | Herzl | |
| 3,952,578 A | 4/1976 | Jacobs | |
| 4,048,853 A | 9/1977 | Smith et al. | |
| 4,080,837 A | 3/1978 | Alexander et al. | 73/61.45 |
| 4,248,085 A | 2/1981 | Coulthard | 73/861.06 |
| 4,320,659 A | 3/1982 | Lynnworth et al. | |
| 4,445,389 A | 5/1984 | Potzick et al. | 73/861.27 |
| 4,520,320 A | 5/1985 | Potzick et al. | |
| 4,561,310 A | 12/1985 | Barnard et al. | |
| 4,677,305 A | 6/1987 | Ellinger | |
| 4,717,159 A | 1/1988 | Alston et al. | |
| 4,883,271 A * | 11/1989 | French | 273/454 |
| 4,896,540 A | 1/1990 | Shakkottai et al. | 73/861.02 |
| 4,932,262 A | 6/1990 | Wlodarczyk | |
| 5,040,415 A | 8/1991 | Barkhoudarian | 73/861.03 |
| 5,083,452 A | 1/1992 | Hope | 73/61 R |
| 5,218,197 A | 6/1993 | Carroll | 250/227.19 |
| 5,285,675 A | 2/1994 | Colgate et al. | 73/23.2 |
| 5,289,726 A | 3/1994 | Miau et al. | |
| 5,359,897 A | 11/1994 | Hamstead et al. | |
| 5,363,342 A | 11/1994 | Layton et al. | |
| 5,367,911 A | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,526,844 A | 6/1996 | Kamen et al. | 137/614.11 |
| 5,591,922 A | 1/1997 | Segeral et al. | 73/861.04 |
| 5,708,211 A | 1/1998 | Jepson et al. | |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,948,959 A | 9/1999 | Peloquin | |
| 6,016,702 A | 1/2000 | Maron | |
| 6,138,512 A | 10/2000 | Roberts et al. | |
| 6,151,958 A | 11/2000 | Letton et al. | 73/61.79 |
| 6,202,494 B1 | 3/2001 | Ricbel et al. | 73/861.29 |
| 6,233,374 B1 | 5/2001 | Ogle et al. | |
| 6,349,599 B1 | 2/2002 | Lynnworth et al. | |
| 6,354,147 B1 | 3/2002 | Gysling et al. | 73/61.79 |
| 6,378,357 B1 | 4/2002 | Han et al. | |
| 6,412,353 B1 | 7/2002 | Kleven et al. | |
| 6,435,030 B1 | 8/2002 | Gysling et al. | |
| 6,442,996 B1 | 9/2002 | Thurston et al. | |
| 6,443,226 B1 | 9/2002 | Diener et al. | |
| 6,449,563 B1 | 9/2002 | Dukhin et al. | |
| 6,450,037 B1 | 9/2002 | McGuinn et al. | |
| 6,463,813 B1 | 10/2002 | Gysling | |
| 6,536,291 B1 | 3/2003 | Gysling et al. | |
| 6,550,342 B2 | 4/2003 | Croteau et al. | 73/800 |
| 6,558,036 B2 | 5/2003 | Gysling et al. | |
| 6,587,798 B2 | 7/2003 | Kersey et al. | 702/50 |
| 6,601,005 B1 | 7/2003 | Eryurek et al. | |
| 6,601,458 B1 | 8/2003 | Gysling et al. | |
| 6,609,069 B2 | 8/2003 | Gysling | |
| 6,658,945 B1 | 12/2003 | Kleven | |
| 6,691,584 B2 | 2/2004 | Gysling et al. | |
| 6,698,297 B2 | 3/2004 | Gysling | |
| 6,732,575 B2 | 5/2004 | Gysling et al. | 73/61.79 |
| 6,782,150 B2 | 8/2004 | Davis et al. | |
| 6,813,962 B2 | 11/2004 | Gysling et al. | 73/861.26 |
| 6,837,098 B2 | 1/2005 | Gysling et al. | 73/61.79 |
| 6,837,332 B1 | 1/2005 | Rodney | |
| 6,862,920 B2 | 3/2005 | Gysling et al. | 73/61.79 |
| 6,889,562 B2 | 5/2005 | Gysling et al. | |
| 6,898,541 B2 | 5/2005 | Gysling et al. | |
| 6,959,604 B2 | 11/2005 | Bryant et al. | |
| 7,032,432 B2 * | 4/2006 | Gysling et al. | 73/24.01 |
| 2001/0020603 A1 | 9/2001 | Moorehead et al. | |
| 2002/0064331 A1 | 5/2002 | Davis et al. | |
| 2002/0123852 A1 | 9/2002 | Gysling et al. | |
| 2002/0129662 A1 | 9/2002 | Gysling et al. | |
| 2003/0038231 A1 | 2/2003 | Bryant et al. | |
| 2003/0089161 A1 | 5/2003 | Gysling | |
| 2003/0136186 A1 | 7/2003 | Gysling et al. | |
| 2003/0154036 A1 | 8/2003 | Gysling et al. | |
| 2004/0006409 A1 | 1/2004 | Liljenberg et al. | |
| 2004/0016284 A1 | 1/2004 | Gysling et al. | |
| 2004/0074312 A1 | 4/2004 | Gysling | |
| 2004/0168523 A1 | 9/2004 | Fernald et al. | |

FOREIGN PATENT DOCUMENTS

| | | | |
|---|---|---|---|
| EP | 0290336 | 11/1988 | |
| GB | 2210169 | 6/1989 | |
| WO | WO93/14382 | 7/1993 | |
| WO | WO99/67629 | 12/1999 | |
| WO | WO 0000793 | 1/2000 | 73/61.79 |
| WO | WO 0102810 | 1/2001 | |

OTHER PUBLICATIONS

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attentuation of Acoustic Waves in Suspensions" by R.L. Gibson, Jr. and M.N. Toksoz.

"Sonar-Based Volumetric Flow Meter for Pulp and Paper Applications" by: Daniel L. Gysling and Douglas H. Loose—Dec. 3, 2002.

"New Flowmeter Principle", by: Walt Boyes—Published in Flow Controls Magazine—Oct. 2003 Issue.

"Piezoelectric Polymers" by: J.S. Harrison—ICASE Report, Dec. 2001.

Sonar-Based Volumetric Flow Meter for Chemical and Petrochemical Applications by: Daniel L. Gysling and Douglas H. Loose—Feb. 14, 2003.

* cited by examiner

APPARATUS AND METHOD FOR MEASURING PARAMETERS OF A MIXTURE HAVING SOLID PARTICLES SUSPENDED IN A FLUID FLOWING IN A PIPE

CROSS-REFERENCE TO RELATED PATENT APPLICATIONS

This application is a continuation in part of U.S. patent application Ser. No. 10/376,427, filed on Feb. 26, 2003, now U.S. Pat. No. 7,032,432, which claimed the benefit of U.S. Provisional Application No. 60/359,785, filed Feb. 26, 2002; and which is a continuation in part of U.S. patent application Ser. No. 10/349,716, filed Jan. 23, 2003, which claims the benefit of U.S. Provisional Application No. 60/351,232, filed Jan. 23, 2002; U.S. Provisional Application No. 60/359,785, filed Feb. 26, 2002; U.S. Provisional Application No. 60/375,847, filed Apr. 24, 2002; U.S. Provisional Application No. 60/425,436, filed Nov. 12, 2002; and U.S. Provisional Application No. 60/426,724, filed Nov. 15, 2002; all of which are incorporated herein by reference in their entirety.

TECHNICAL FIELD

This invention relates to an apparatus for measuring the flow passing within a pipe, and more particularly to an apparatus and method for measuring the speed of sound propagating in the flow, having particles suspended within a continuous fluid, to determine parameters, such as particle/fluid ratio, particle size and volumetric flow rate of the flow in pipes using acoustic dynamic pressures.

BACKGROUND ART

This invention provides a method to measure parameters of a fluid/particle mixture in a pipe that can be used in many applications, such as in chemical, pharmaceutical, petroleum and power generation industries. In particular, the invention provides a method to measure pulverized coal and air mixtures used in pulverized fuel delivery systems in place in a large percentage of coal fired boilers used in the power generation industry.

Currently, well over 50% of the electricity in the US is generated with coal. While coal is considered a cost effective, abundant resource in the US, the use of coal has been restricted due in large part to environmental concerns. To mitigate this impact, the US Department of Energy and the Power Generation industry have large programs designed to develop technology to reduce the environment effects of burning coal. These Clean Coal Initiatives include technology designed to develop improvements in the combustion process to improve efficiency while reducing pollutants such as unburned carbon, ash, and nitrous oxide (NOx).

The ability to measure the flow rate and composition of the air/coal mixture within the coal pipes is an important aspect of any system or strategy designed to optimize the performance of the PF delivery system. The industry recognizes this and therefore has been developing a wide variety of technologies to perform this measurement. These include probe based and sampling devices, as well as real time meters based on a wide variety of technologies including electrostatic charges, microwaves, and ultrasonic.

SUMMARY OF THE INVENTION

Objects of the present invention include providing a system for measuring the speed of sound propagating through a particle/fluid mixture in pipes in industrial boiler systems and related processes, such as coal fired boiler systems, to determine particular parameters of the mixture.

According to the present invention, an apparatus for measuring at least one parameter of a particle/fluid mixture in a pipe includes a spatial array of at least two pressure sensors, disposed at different axial locations along the pipe. Each of the pressure sensors measures an unsteady pressure within the pipe at a corresponding axial location. Each of said sensors provides a pressure signal indicative of the unsteady pressure within the pipe at said axial location of a corresponding one of said sensors. A signal processors responsive to said pressure signals, provides a signal indicative of the at least one parameter of the mixture in the pipe.

According to the present invention, a method for measuring at least one parameter of a particle/fluid mixture in a pipe includes measuring unsteady pressures within the pipe at at least two predetermined axial measurement locations along the pipe to provide a pressure signal indicative of the unsteady pressure within the pipe at each of the at least two predetermined axial measurement locations. Further the method includes calculating the at least one parameter of the particle/fluid mixture in the pipe using the unsteady pressure measured at the axial measurement locations.

The foregoing and other objects, features and advantages of the present invention will become more apparent in light of the following detailed description of exemplary embodiments thereof.

BEST MODE FOR CARRYING OUT THE INVENTION

Figure 1:
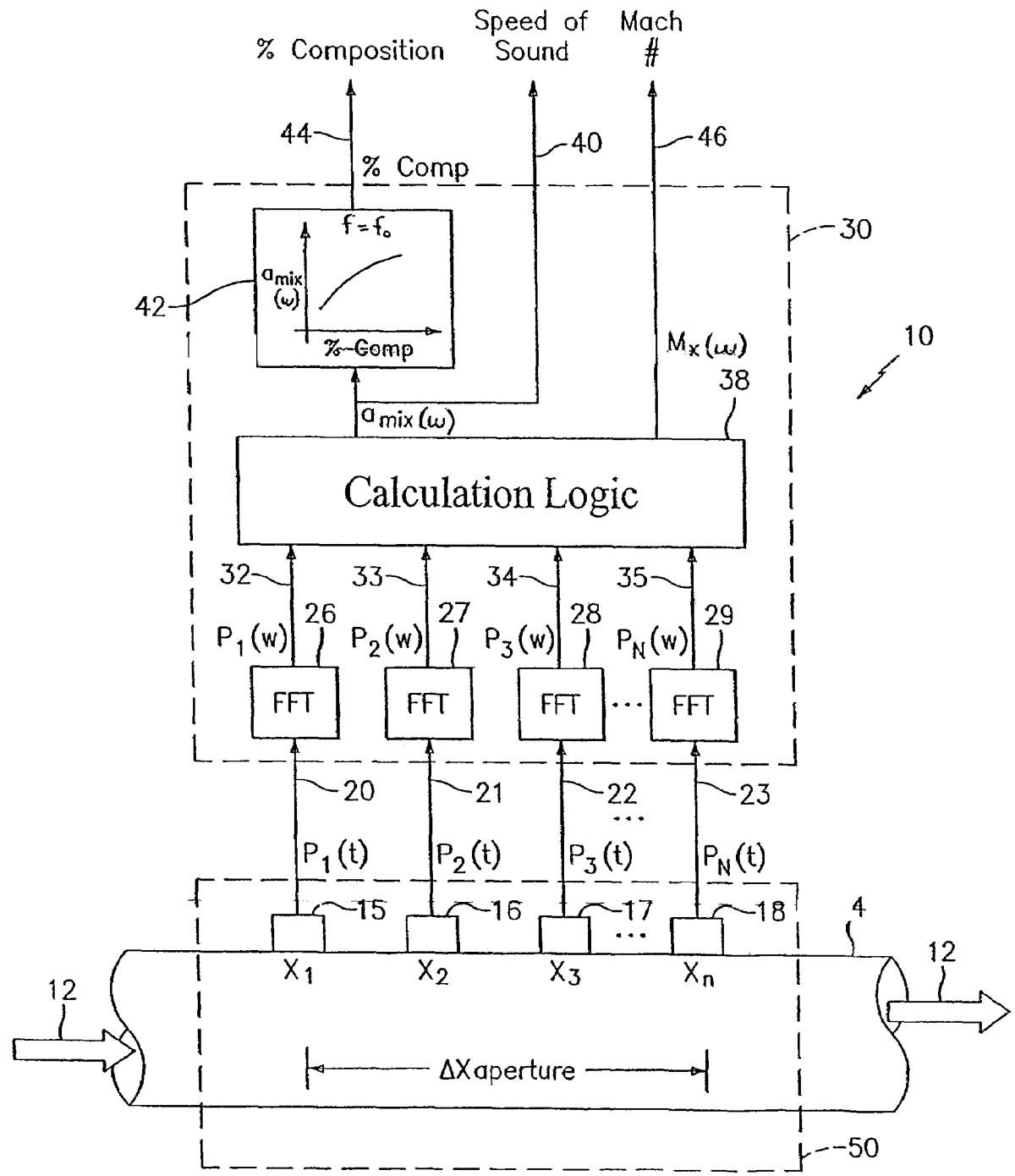
FIG. 1 is a block diagram of a flow meter for measuring the speed of sound of the fluid/particle mixture flowing with a pipe, in accordance with the present invention.

Referring to FIG. 1, a flow meter 10 embodying the present invention is provided that measures a number of parameters/characteristics of a mixture 12 of solid particles suspended within a continuous fluid flowing within a pipe or conduit 14, wherein a fluid is defined as a liquid and/or a gas. The flow meter may be configured and programmed to measure the speed of sound propagating through the mixture. The flow meter can measure at least one of the following parameters of the mixture flow 12: the fluid/particle concentration (volumetric phase fraction), the volumetric flow rate, the size of the solid particles, the mass flow of the mixture and the velocity of the mixture. To determine any one of these parameters, the flow meter 10 measures the unsteady pressures created by the speed of sound (SOS) propagating through the mixture flowing in the pipe 14, which will be described in greater detail hereinafter.

The solid particles of the mixture 12 may be of any size, shape and material. For example, the particles may be small in size as in the form of a powder, in a granular form, or greater in size. The flow meter 10 can be used in any application that carries solid particles suspended in a fluid through a pipe, such as in chemical, pharmaceutical, petroleum and power generation applications. For example, the present invention is well suited to measure the parameters (e.g. air/coal ratio, particle size) for power generation systems that use pulverized coal to fire the furnace a steam boiler system.

Figure 2:
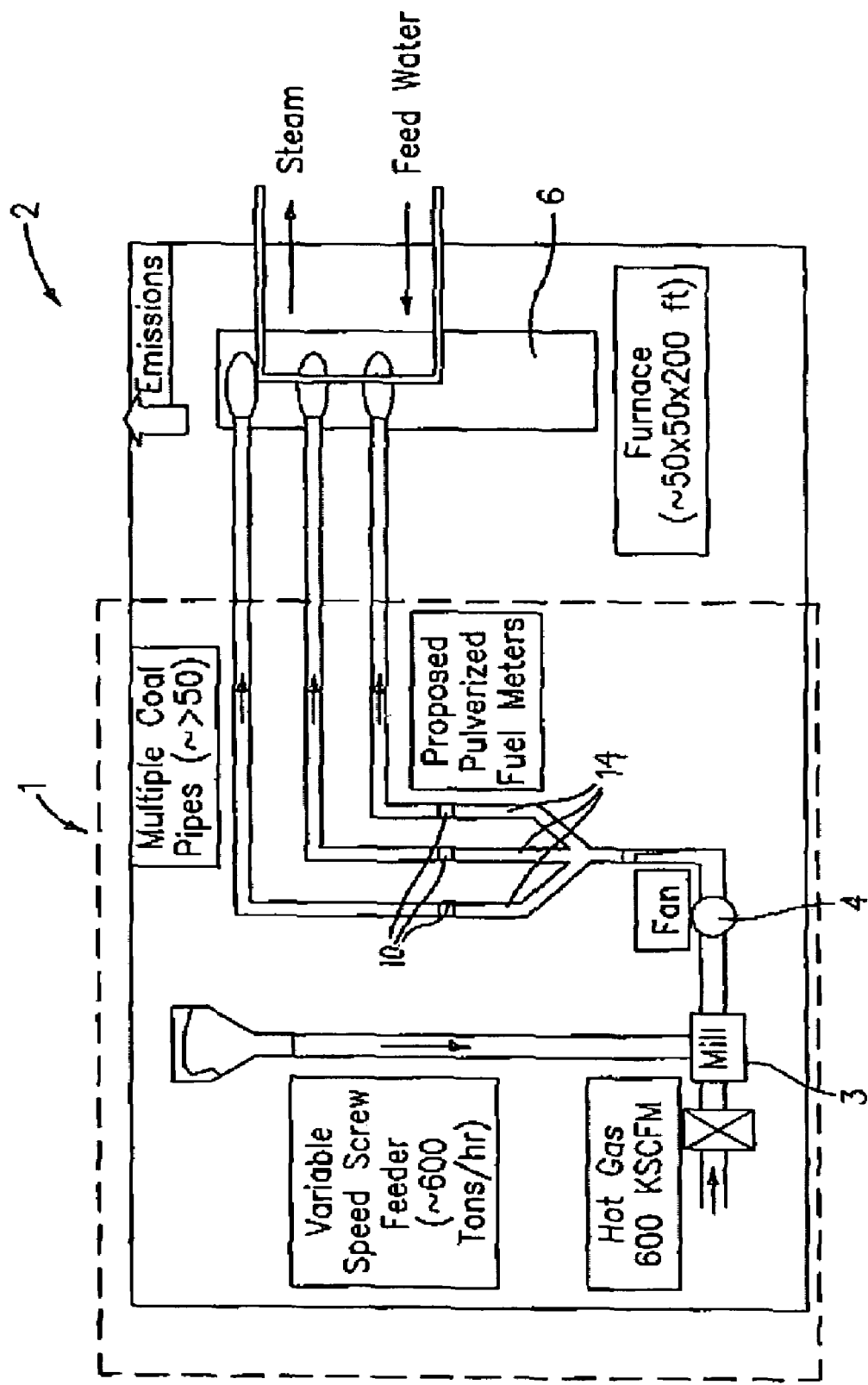
FIG. 2 is a schematic diagram of a pulverized fuel (PF)/air mixture parameter measurement system within a coal fired boiler system, in accordance with the present invention.

As one example, the present invention will be discussed in the context of a Pulverized Fuel (PF) delivery system for power generation, but one will appreciate that the flow meter can be applied to any number of other applications, as discussed hereinbefore. A representative PF delivery system 1 is shown in a coal fired boiler system 2 in FIG. 2. The coal is pulverized in a mill 3 and entrained in air produced by many means, such as a fan 4 to transport the PF/air mixture via pipes 12 for delivery to the furnace 6. Typical furnaces can have greater than fifty coal pipes, each twelve to 20 inches in diameter. Typically, a large utility boiler >300 Mw, can have four to eleven pulverizing mills feeding the furnace. The ability of the PF delivery system to deliver the proper amount of fuel and air to the furnace through these multiple coal pipes, both collectively and individually, has a strong influence on the performance and emissions from the coal fired boiler.

As is known, non-uniformities in the PF delivery system 1 can result in variation of the fuel to air ratios, causing hot spots, regions of high NOx generation, and unburned fuel. The connection between performance of a PF fuel delivery system 1 and boiler system 2 is well recognized. The flow meter 10 embodying the present invention is capable of measuring the fuel to air ratio and particle size of the pulverized coal provided to the furnace to thereby provide feedback to the operator to provide more efficient combustion of the coal.

As described hereinbefore, the flow meter 10, of the present invention may be configured and programmed to measure and process the detected unsteady pressures $P_1(t)$-$P_N(t)$ created by acoustic waves propagating through the mixture to determine parameters of the mixture flow 12. One such flow meter 10 is shown in FIG. 1 that measures the speed of sound (SOS) of one-dimensional sound waves propagating through the fluid/particle mixture to determine the composition the mixture, namely the liquid/particle ratio of the mixture. The flow meter is also capable of determining the average size of the particles, velocity of the mixture, and the volumetric flow rate of the mixture. It is known that sound propagates through various mediums at various speeds in such fields as SONAR and RADAR fields. The speed of sound of a mixture within a pipe 14 may be determined using a number of known techniques, such as those set forth in U.S. Pat. No. 6,354,147, entitled "Fluid Parameter Measurement in Pipes Using Acoustic Pressures", issued Mar. 12, 2002, and U.S. patent application Ser. No. 10/007,749, entitled "Fluid Parameter Measurement in Pipes Using Acoustic Pressures", filed Nov. 7, 2001, now U.S. Pat. No. 6,732,575, each of which are incorporated herein by reference. The present invention utilizes at least one flow meter 10 to determine various parameters of the liquid/particle mixture, wherein one of the parameters is the speed at which sound travels within the mixture pipe system as will be more fully described herein below.

In accordance with the present invention, the speed of sound propagating through the mixture 12 is measured by passively listening to the flow with an array of unsteady pressure sensors to determine the speed at which one-dimensional compression waves propagate through the liquid/particle mixture contained within the pipe 14.

As shown in FIG. 1, the flow meter 10 has an array of at least three acoustic pressure sensors 15,16,17, located at three locations $x_1,x_2,x_3$ axially along the pipe 14. One will appreciate that the sensor array may include more than three pressure sensors as depicted by pressure sensor 18 at location $x_N$. The pressure generated by the acoustic waves may be measured through holes in the pipe 14 reported external pressure sensors 15-18 or by other techniques discussed hereinafter. The pressure sensors 15-18 provide pressure time-varying signals $P_1(t),P_2(t),P_3(t),P_N(t)$ on lines 20,21, 22,23 to a signal processing unit 30 to known Fast Fourier Transform (FFT) logics 26,27,28, 29, respectively. The FFT logics 26-29 calculate the Fourier transform of the time-based input signals $P_1(t)$-$P_N(t)$ and provide complex frequency domain (or frequency based) signals $P_1(\omega),P_2(\omega)$, $P_3(\omega),P_N(\omega)$ on lines 32,33,34,35 indicative of the frequency content of the input signals. Instead of FFT's, any other technique for obtaining the frequency domain characteristics of the signals $P_1(t)$-$P_N(t)$, may be used. For example, the cross-spectral density and the power spectral density may be used to form a frequency domain transfer functions (or frequency response or ratios) discussed hereinafter.

The frequency signals $P_1(\omega)$-$P_N(\omega)$ are fed to $a_{mix}$-Mx Calculation Logic 38 which provides a signal to line 40 indicative of the speed of sound propagating through the mixture $a_{mix}(\omega)$, which is a function frequency (discussed more hereinafter). The $a_{mix}(\omega)$ signal is provided to map (or equation) logic 42, which converts $a_{mix}(\omega)$ to a percent composition of the PF/air mixture and provides a % Comp signal to line 44 indicative thereof (as discussed hereinafter). Also, if the Mach number Mx($\omega$) is not negligible and is desired, the calculation logic 38 may also provide a signal Mx($\omega$) to line 46 indicative of the Mach number Mx($\omega$) which is a function of frequency.

For circular ducts or pipes 14 as shown in FIG. 1, only plane waves propagate for frequencies below the cut-on frequency (ref Acoustics of Ducts and Mufflers, M.J. Munjal, John Wiley & Sons, New York, 1987):

$$f < \frac{1.84}{\pi D} a$$

For a mixture with a sound speed of 500 m/sec in an eighteen inch pipe, the cut-off frequency is approximately 600 Hz. Thus, for this example, only one-dimensional acoustic waves propagate below 600 Hz. It is important to note that one-dimensional waves can still propagate above this frequency, but higher order modes may or may not be present.

More specifically, for planar one-dimensional acoustic waves in a homogenous mixture, it is known that the acoustic pressure field P(x,t) at a location x along a pipe, where the wavelength $\lambda$ of the acoustic waves to be measured is long compared to the diameter d of the pipe 14 (i.e., $\lambda/d \gg 1$), may be expressed as a superposition of a right traveling wave and a left traveling wave, as follows:

$$P(x,t)=(Ae^{-ik_r x}+Be^{+ik_l x})e^{i\omega t} \quad \text{Eq. 1}$$

where A,B are the frequency-based complex amplitudes of the right and left traveling waves, respectively, x is the pressure measurement location along a pipe, $\omega$ is frequency (in rad/sec, where $\omega=2\pi f$), and $k_r, k_l$ are wave numbers for the right and left travelling waves, respectively, which are defined as:

$$k_r \equiv \left(\frac{\omega}{a_{mix}(\omega)}\right)\frac{1}{1+M_x(\omega)} \text{ and}$$

$$k_l \equiv \left(\frac{\omega}{a_{mix}(\omega)}\right)\frac{1}{1-M_x(\omega)} \quad \text{Eq. 2}$$

where $a_{mix}(\omega)$ is the speed of sound of the mixture in the pipe, $\omega$ is frequency (in rad/sec), and $M_x(\omega)$ is the axial Mach number of the flow of the mixture within the pipe, where:

$$M_x(\omega) \equiv \frac{V_{mix}}{a_{mix}(\omega)} \quad \text{Eq. 3}$$

where Vmix is the axial velocity of the mixture. For non-homogeneous mixtures, the axial Mach number represents the average velocity of the mixture and the low frequency acoustic field description remains substantially unaltered.

The frequency domain representation P(x,$\omega$) of the time-based acoustic pressure field P(x,t) Within a pipe, is the coefficient of the $e^{i\omega t}$ term of Eq. 1, as follows:

$$P(x,\omega)=Ae^{-ik_r x}+Be^{+ik_l x} \quad \text{Eq. 4}$$

Referring to FIG. 1, we have found that using Eq. 4 for P(x,$\omega$) at three axially distributed pressure measurement locations $x_1, x_2, x_3$ along the pipe 14 leads to an equation for $a_{mix}$ as a function of the ratio of frequency based pressure measurements, which allows the coefficients A,B to be eliminated. For optimal results, A and B are substantially constant over the measurement time and substantially no sound (or acoustic energy) is created or destroyed in the measurement section. The acoustic excitation enters the test section only through the ends of the test section 50 and, thus, the speed of sound within the test section 50 can be measured independent of the acoustic environment outside of the test section. In particular, the frequency domain pressure measurements $P_1(\omega), P_2(\omega), P_3(\omega)$ at the three locations $x_1, x_2, x_3$, respectively along the pipe 14 using Eq. 1 for right and left traveling wvaes as follows:

$$P_1(\omega)=P(x=x_1,\omega)=Ae^{-ik_r x_1}+Be^{+ik_l x_1} \quad \text{Eq. 5}$$

$$P_2(\omega)=P(x=x_2,\omega)=Ae^{-ik_r x_2}+Be^{+ik_l x_2} \quad \text{Eq. 6}$$

$$P_3(\omega)=P(x=x_3,\omega)=Ae^{-ik_r x_3}+Be^{+ik_l x_3} \quad \text{Eq. 7}$$

where, for a given frequency, A and B are arbitrary constants describing the acoustic field between the sensors 15,16,17. Forming the ratio of $P_1(\omega)/P_2(\omega)$ from Eqns. 6, 7, and solving for B/A, gives the following expression:

$$R \equiv \frac{B}{A} = \frac{e^{-ik_r x_1} - \left[\frac{P_1(\omega)}{P_2(\omega)}\right]e^{-ik_r x_2}}{\left[\frac{P_1(\omega)}{P_2(\omega)}\right]e^{-ik_l x_2} - e^{-ik_l x_1}} \quad \text{Eq. 8}$$

where R is defined as the reflection coefficient.

Forming the ratio of $P_1(\omega)/P_3(\omega)$ from Eqs. 5 and 7 and solving for zero gives:

$$\frac{e^{-ik_r x_1}+Re^{ik_l x_1}}{e^{-ik_r x_3}+Re^{ik_l x_3}} - \left[\frac{P_1(\omega)}{P_2(\omega)}\right] = 0 \quad \text{Eq. 9}$$

where R=B/A is defined by Eq. 8 and kr and kl are related to $a_{mix}$ as defined by Eq. 2. Eq. 9 may be solved numerically, for example, by defining an "error" or residual term as the magnitude of the left side of Eq. 9, and iterating to minimize the error term.

$$mag\left[\frac{e^{-ik_r x_1}+Re^{ik_l x_1}}{e^{-ik_r x_3}+Re^{ik_l x_3}} - \left[\frac{P_1(\omega)}{P_2(\omega)}\right]\right] \equiv \text{Error} \quad \text{Eq. 10}$$

The data from the array of sensors may be processed in any domain, including the frequency/spatial domain, the temporal/spatial domain, the temporal/wave-number domain or the wave-number/frequency (k-$\omega$) domain. As such, any known array processing technique in any of these or other related domains may be used if desired.

Also, some or all of the functions within the signal processing unit 30 may be implemented in software (using a microprocessor or computer) and/or firmware, or may be implemented using analog and/or digital hardware, having sufficient memory, interfaces, and capacity to perform the functions described herein.

Acoustic pressure sensors 15-18 sense acoustic pressure signals that, as measured, are lower frequency (and longer wavelength) signals than those used for ultrasonic flow meters of the prior art, and thus the current invention is more tolerant to inhomogeneities in the flow, such as roping and other time and space domain inhomogeneities within the flow, even where entrenchment or coal "roping" is unlikely such as following a bend. The term "roping" is a term known to those skilled in this art which represents a form of severe spatial and temporal mal-distribution induced in mixture flows of widely different component densities. It is a condition where a large portion of the coal flow is in a band running along one side of pipe 14.

In addition, the present invention incorporates the compliance of the pipe 14 to determine the effective speed of sound of the pipe/PF/air mixture system. The acoustic pressure signals $P_1(t)-P_N(t)$ are generated within the PF/air mixture of the pipe 14 by a variety of non-discrete sources such as remote machinery, mills, fans 4 (FIG. 2), valves, elbows, as well as the PF/air mixture flow itself. It is this last source, the PF/air mixture 12 flowing within the pipe 14, which is a generic source of acoustic noise that assures a minimum level of acoustics for any PF/air mixture piping systems for which the present invention takes unique advantage. The flow generated acoustics increase with mean flow velocity and the overall noise levels (acoustic pressure levels) are a function of the generating mechanism and the damping mechanism. As such, no external discrete noise source is required within the present invention and thus may operate using passive listening. While the flow meter 10 passively listens to the mixture flow 12, the present invention contemplates adding an acoustic source to inject a desire acoustic wave into the flow to be measured, such as by compressing, vibrating and/or tapping the pipe, to name a few examples.

For certain types of pressure sensors, e.g., pipe strain sensors, accelerometers, velocity sensors or displacement sensors, discussed hereinafter, it may be desirable for the pipe 14 to exhibit a certain amount of pipe compliance.

Alternatively, to minimize any error effects (and the need for the corresponding calibration) caused by pipe compliance, the axial test section 50 of the pipe 14 along where the sensors 15-18 are located may be made as rigid as possible. To achieve the desired rigidity, the thickness of the wall of the test section 50 may be made to have a predetermined thickness, or the test section 50 may be made of a very rigid material, e.g., steel, titanium, Kevlar®, ceramic, or other material with a high modulus.

The length of the array (aperture) ΔX of the pressure sensors (15-18) is at least a significant fraction of the measured wavelength of the acoustic waves being measured. As will be described in greater detail, the acoustic wavelength to be measured is a function of at least the dispersion characteristics of the mixture 12, wherein the dispersion characteristic is a function of at least the size and mass of the particles, and the viscosity of the fluid. The greater the dispersion of the mixture (e.g. the greater the size and mass, and/or the less viscous the fluid), the longer the length of the array is needed. Conversely, the lesser the dispersion of the mixture (e.g. the lesser the size and mass, and/or the more viscous the fluid), the shorter the length of the array is needed.

Further, it is within the scope of the present that the spacing of the pressure sensors may be known or arbitrary, provided the location of the sensors is known. The sensors 15-18 may also be equi-spaced (as shown in FIG. 1) or any non-even or non equi-spaced location, as will be described in greater detail hereinafter. One will appreciate that as few as two sensors are required if certain information is known about the acoustic properties of the PF/air mixture piping system.

As discussed, the flow meter 10 measures the speed of sound of one-dimensional sound waves propagating through the fluid/particle mixture to determine the composition of the mixture. Specifically, the speed of sound propagating through dilute solid/air mixtures can be directly related to the mass fraction particles of the flow. A typical PF fuel delivery system 1 may operate with an air to coal mass ratio of 1.5 to 2.5 with coal density of 1200 to 1400 kg/m$^3$ compared to 1.2 kg/m$^3$ for air at standard atmospheric conditions. Thus, meeting the desired mass ratio results in a very dilute mixture of coal on a volumetric basis, on the order of one part in 1000 by volume.

Assuming that the particles of coal are small enough and the acoustic frequencies and the frequencies of perturbations associated with the acoustics are low enough for the solid particles to exhibit negligible slip (both steady and unsteady), the sound speed can be assumed to be non-dispersive (that is constant with frequency) and the volumetric phase fraction of the mixture could be determined through the Wood equation:

$$\rho_{mix} = \sum_{i=1}^{N} \phi_i \rho_i$$

$$\frac{1}{\rho_{mix} a_{mix}^2} = \sum_{i=1}^{N} \frac{\phi_i}{\rho_i a_i^2}$$

$$\sum_{i=1}^{N} \phi_i = 1$$

Including the effect of the compliance introduced by the conduit 12 (in this case a circular pipe of modulus E, radius R and wall thickness t)

$$\frac{1}{\rho_{mix} a_{measured}^2} = \frac{1}{\rho_{mix} a_{mix}^2} + \sigma \text{ where } \sigma \equiv \frac{2R}{Et}$$

Figure 4:
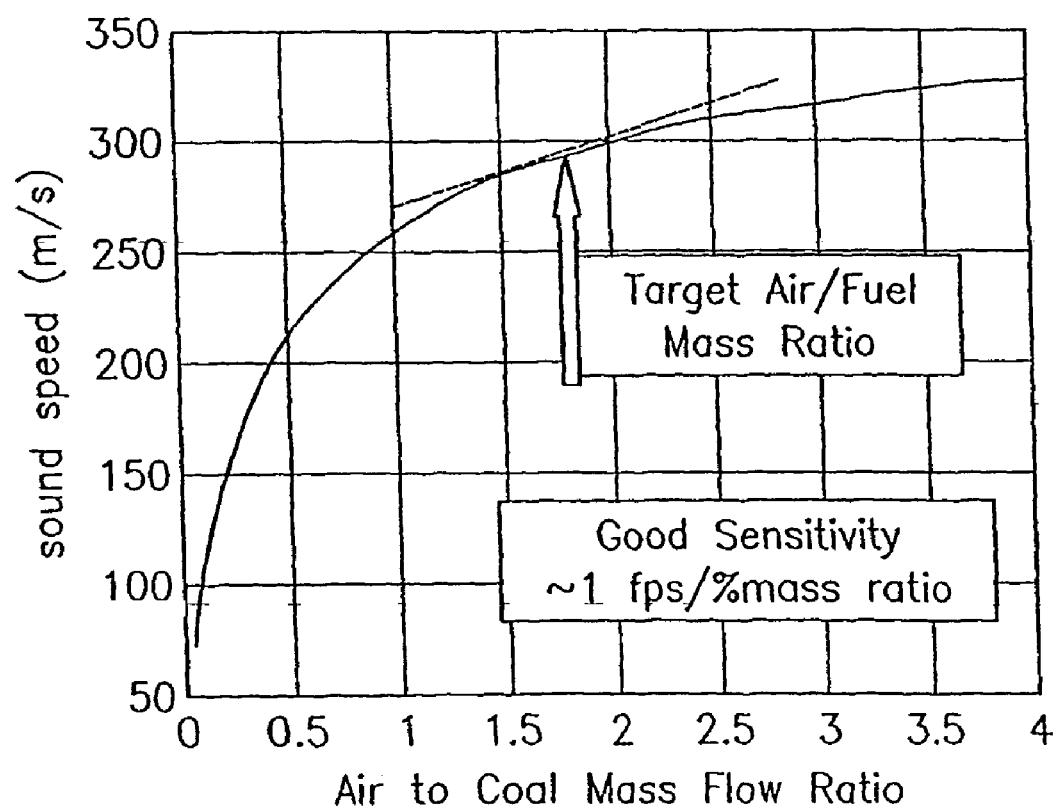
FIG. 4 is a plot of the speed of sound of a mixture versus the frequency in air/coal mass flow ratio, in accordance with the present invention.

Utilizing the relations above, the speed at which sound travels within the piping system of a representative coal/air mixtures is shown in FIG. 4 as a function of air/coal mass ratio. For this example, the pure air was assumed to have a density of 1.2 kg/m^3 and a sound speed of 365.9 m/s and the coal was assumed to have a density of 1400 kg/m^3 and a sound speed of 2439 m/s. As shown, the effect of increasing coal fraction, i.e. decreasing air/coal ratio is to decrease the sound speed. Physically, adding coal particles effectively mass loads the mixture, while not appreciably changing the compressibility of the air. Over the parameter range of interest, the relation between mixture sound speed and air/coal ratio is well behaved and monatomic.

While the calibration curves based on predictions from first principles are encouraging, using empirical data mapping from sound speed to air/coal ratio may result in improved accuracy of the present invention to measure the air/coal fractions of the mixture.

Figure 7:
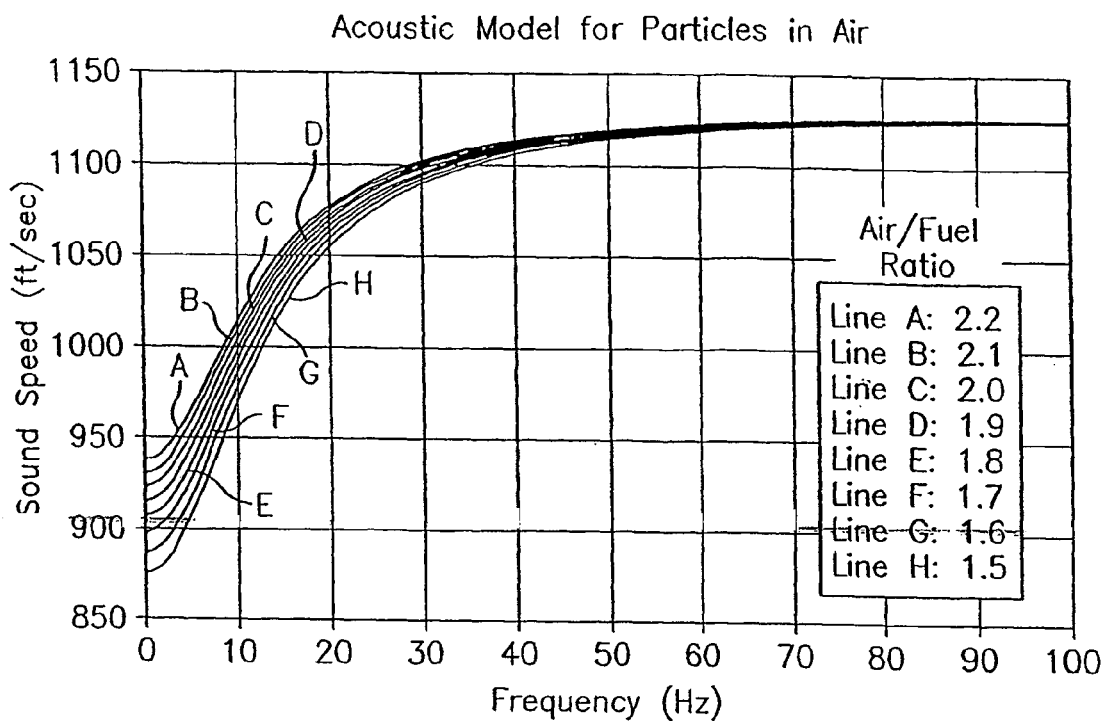
FIG. 7 is a plot of sound speed as a function of frequency for air/coal mixtures with fixed particle size (50 mm) and varying air-to-fuel mass ratio in accordance with the present invention.
Figure 8:
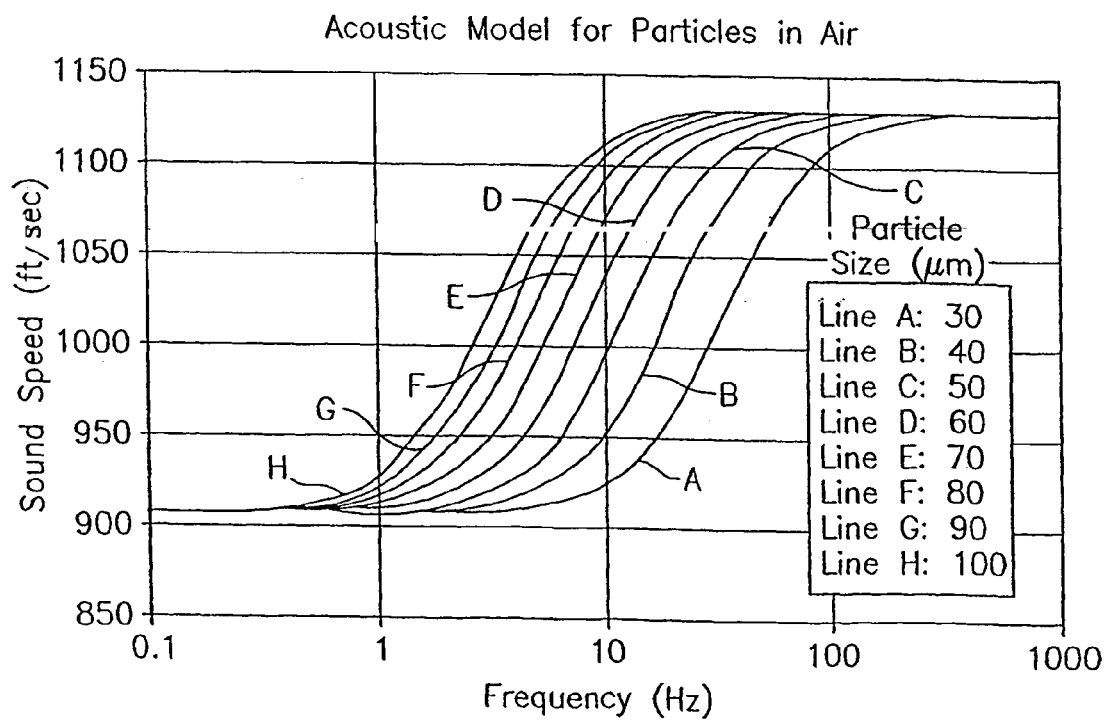
FIG. 8 is a plot of sound speed as a function of frequency for air/coal mixtures with varying particle size where the air-to-fuel mass ratio is equal to 1.8 in accordance with the present invention.

However, it has been discovered that the physical properties of pulverized coal/air mixtures are generally such that there will be velocity slip at all but very low frequencies (on the order of <1-2 Hz for nominally 50 µm coal particles in air), as shown in FIGS. 7 and 8 which will described in greater detail hereinafter.

Figure 3:
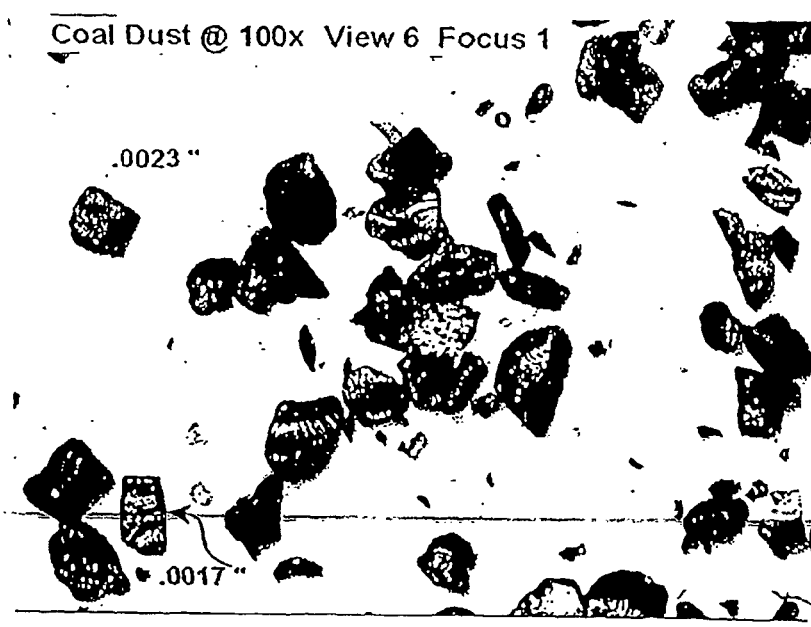
FIG. 3 is a magnified photograph showing particle size of coal typical of the system shown in FIG. 2.
Figure 5:
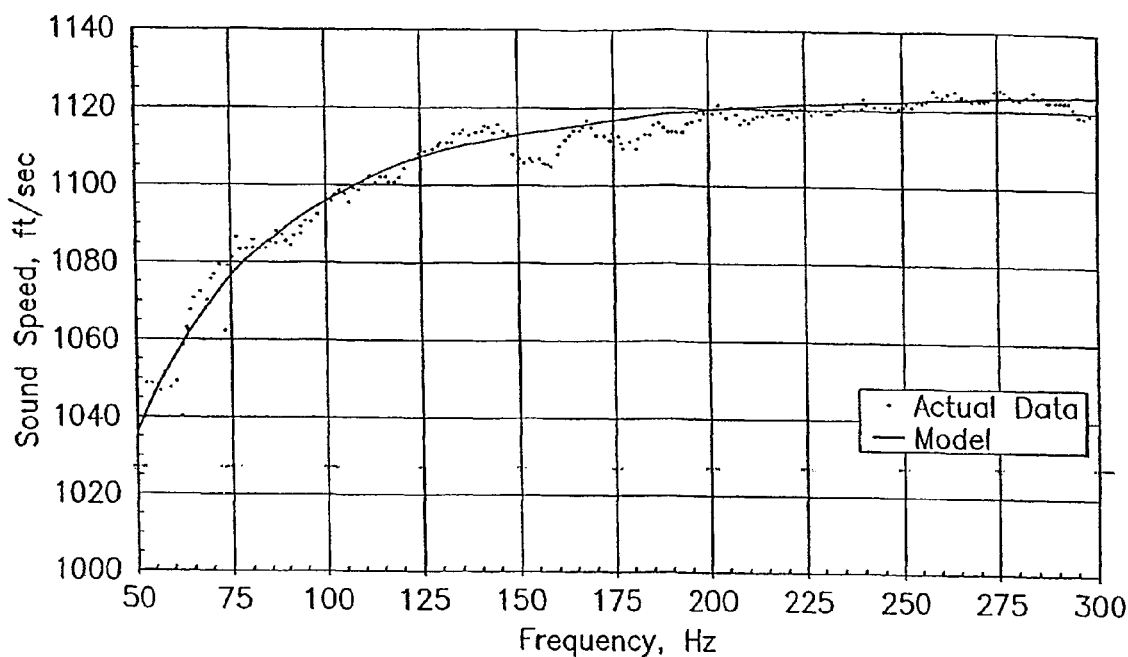
FIG. 5 is a plot of actual data and a model of the speed of sound as a function of frequency for air/coal mixtures, in accordance with the present invention.

FIG. 5 shows the measured speed of sound as a function of frequency for an actual coal/air mixture 12. The sound speed was measured utilizing passive listening techniques of the present invention as described herein. The frequency dependence of the sound speed was determined by applying a Capon array-processing algorithm at multiple narrow frequency ranges between 50-300 Hz thereby determining a frequency specific acoustic propagation velocity. In this particular example, the data was obtained wherein the coal/air mixture was flowing at nominally 100 ft/sec with an air-to-coal mass ratio equal to 1.8. The coal particles were nominally 50 µm in size, representative of pulverized coal typically used in power generation and other industrial applications. A magnified view of the coal particles that were used for this test is shown in FIG. 3.

Further shown in FIG. 5, the sound speed increases with increasing frequency and asymptotes toward a constant value. The sound speed asymptote at higher frequencies is essentially the sound speed propagating through air only with no influence of the suspended particles. Also, it is apparent that the sound speed of the coal/air mixture has not reached the quasi-steady limit at the lowest frequency for which sound speed was measured. The sound speed is continuing to decrease at the lower frequency limit. An important discovery of the present invention is that the speed at which sound propagates through dilute particles suspended in a continuous fluid is said to be dispersive. As defined herein, the speed at which acoustic waves propagate through dispersive mixtures varies with frequency.

Figure 6:
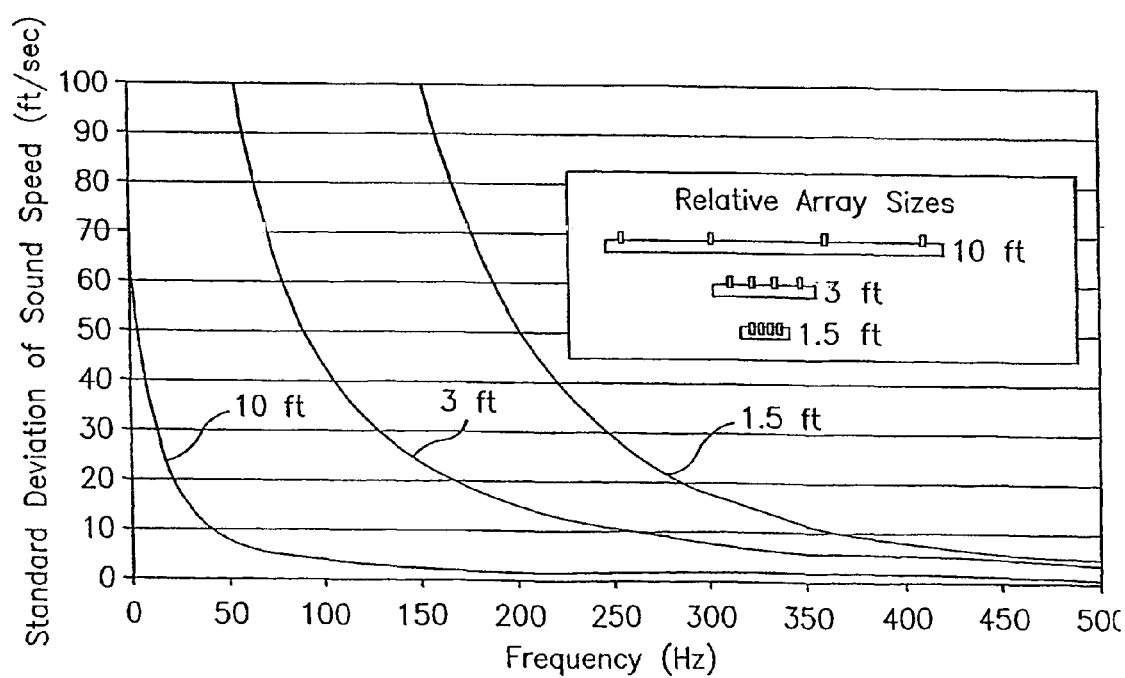
FIG. 6 is a plot showing the standard deviation of sound speed versus frequency for various arrays of a PF/air mixture parameter measurement system, in accordance with the present invention.

Measuring the sound speed of a mixture 12 at progressively lower and lower frequencies becomes inherently less accurate as the total length of the array of pressure sensors 15-18 ($\Delta x_{operature}$), which define the aperature of the array, becomes small compared to the wavelength of the acoustics. In general, the aperture should be at least a significant fraction of a wavelength of the sound speed of interest. In a particular embodiment sound speed data was recorded with an array of four sensors, spaced at twelve inches, for a total aperture of three feet. At 50Hz, a 1000 ft/sec sound wave has a wavelength of 20 ft. Thus, the aperture of this particular array (approx. thirty-six inches) spanned only 3/20ths of a wavelength, and the array's ability to accurately resolve sound speeds below this was clearly impaired. It is an important aspect of the present invention that the ability to resolve sound speed at low frequencies is directly related to aperture of the may. Consequently longer arrays are used to resolve sound speeds at lower frequencies. As shown in FIG. 6, the standard deviation associated with determining the speed of sound in air is shown as a function of frequency for three arrays of varying aperture, namely 1.5 ft. 3 ft and 10 ft.

Given the practical constraints in accurately measuring sound speeds at ultra-low frequencies, the data suggests that utilizing a quasi-steady model to interpret the relationship between sound speed, measured at frequencies above those at which the quasi-steady model is applicable, and the air-to-fuel ratio would be problematic, and may, in fact, be impractical. Thus, the key to understanding and interpreting the composition of coal/air mixtures through sound speed measurements lies in the dispersive characteristics of the coal/air mixture.

In accordance with the present invention the dispersive nature of the system utilizes a first principles model of the interaction between the air and particles. This model is viewed as being representative of a class of models that seek to account for dispersive effects. Other models could be used to account for dispersive effects without altering the intent of this disclosure (for example, see the paper titled "Viscous Attenuation of Acoustic Waves in Suspensions" by R. L. Gibson, Jr. and M. N. Toksöz), which is incorporated herein by reference. The model allows for slip between the local velocity of the continuous fluid phase and that of the particles. The drag force on the particles by the continuous fluid is modeled by a force proportional to the difference between the local fluid velocity and that of the fluid particles and is balanced by inertial force:

$$F_{drag} = K(U_f - U_p) = \rho_p v_p \frac{\partial U_p}{\partial t}$$

where K=proportionality constant, $U_f$=fluid velocity, $U_p$=particle velocity, $\rho_p$=particle density and $v_p$=particle volume.

The effect of the force on the continuous fluid phase by the fluid particles is modeled as a force term in the axial momentum equation. The axial momentum equation for a control volume of area A and length $\Delta x$ is given by:

$$P_x - P_{x+\Delta x} - K(U_f - U_p)\left\{\frac{\phi_p \Delta x}{v_p}\right\} = \frac{\partial}{\partial t}(\rho_f U_f \Delta x)$$

where P=pressure at locations x and $\Delta x$, $\phi_p$=volume fraction of the particles, $\rho_f$=fluid density.

The particle drag force is given by:

$$F_{drag} = K(U_f - U_p) = C_d A_p \frac{1}{2}\rho_f (U_f - U_p)^2$$

where $C_d$=drag coefficient, $A_p$=frontal area of particle and $\rho_f$=fluid density.

Using Stokes law for drag on a sphere at low Reynold's number gives the drag coefficient as:

$$C_d = \frac{24}{Re} = \frac{24\mu}{\rho_f (U_f - U_p) D_p}$$

where $D_p$=particle diameter and $\mu$=fluid viscosity.

Solving for K in this model yields:

$$K = 3\pi\mu D_p$$

Using the above relations and 1-dimensional acoustic modeling techniques, the following relation can be derived for the dispersive behavior of an idealized fluid particle mixture.

$$a_{mix}(\omega) = a_f \sqrt{\frac{1}{1 + \dfrac{\varphi_p \rho_p}{\rho_f\left(1 + \omega^2 \dfrac{\rho_p^2 v_p^2}{K^2}\right)}}}$$

In the above relation, the fluid SOS, density ($\rho$) and viscosity ($\phi$) are those of the pure phase fluid, $v_p$ is the volume of individual particles and $\phi_p$ is the volumetric phase fraction of the particles in the mixture.

Two parameters of primary interest in pulverized coal measurements are particle size and air-to-fuel mass ratio. To this end, it is of interest to examine the dispersive characteristics of the mixture as a function of these two variables. FIGS. 7 and 8 show the dispersive behavior for coal/air mixtures with parameters typical of those used in pulverized coal deliver systems.

In particular FIG. 7 shows the predicted behavior for nominally 50 µm size coal in air for a range of air-to-fuel ratios. As shown, the effect of air-to-fuel ratio is well defined in the low frequency limit. However, the effect of the air-to-fuel ratio becomes indistinguishable at higher frequencies, approaching the sound speed of the pure air at high frequencies (above ~100 Hz).

Similarly, FIG. 8 shows the predicted behavior for a coal/air mixture with an air-to-fuel ratio of 1.8 with varying particle size. This figure illustrates that particle size has no influence on either the low frequency limit (quasi-steady) sound speed, or on the high frequency limit of the sound speed. However, particle size does have a pronounced effect in the transition region.

FIGS. 7 and 8 illustrate an important aspect of the present invention. Namely, that the dispersive properties of dilute mixtures of particles suspended in a continuous fluid can be broadly classified into three frequency regimes: low frequency range, high frequency range and a transitional frequency range. As best shown in FIG. 8, the speed of sound propagating through the mixture is substantially the same regardless of the particle size in the low frequency range. In the low frequency range the mixture exhibits a quasi-steady model or a no slip (non-dispersive) characteristic. As shown in the intermediate frequency range, the speed of sound propagating through the mixture is dependent on the size of the particle, and thus exhibits dispersive characteristics. For the high frequency range, the speed of sound propagating through the mixture is unaffected by the particles. In other words, the speed of sound in the higher frequency range propagating through the mixture is substantially equally to the speed of sound propagating through the just the fluid with the particles having no effect, which will be described in greater detail hereinafter.

Knowing the effect of dispersion on the speed of sound through a mixture as described herein before, one will appreciate that to determine the concentration of the mixture (e.g., air/fuel ratio), the frequency of the measured acoustic wave is within the low frequency range that exhibits little or no slip (non-dispersive/quasi-steady state), as best shown in FIG. 7. Further, one will appreciate that to determine the particle size within the mixture 12, the frequency of the measured acoustic wave is within the intermediate frequency range that exhibits dispersive characteristics, as shown in FIG. 8.

Although the effect of particle size and air-to-fuel ratio are inter-related, the predominant effect of air-to-fuel ratio is to determine the low frequency limit of the sound speed to be measured and the predominate effect of particle size is to determine the frequency range of the transitional regions. As particle size increases, the frequency at which the dispersive properties appear decreases. For typical pulverized coal applications, this transitional region begins at fairly low frequencies, ~2 Hz for 50 µm size particles.

In the low frequency regime, the particles exhibit negligible slip with the fluid. The frequency range for which the no-slip, quasi-steady approximation is valid is a function of a variety of parameters including particle size, continuous phase viscosity, particle shape and particle density.

The quasi-steady (no-slip condition) sound speed is given by the low frequency limit of the above relation, where AFR is air/fuel ratio:

$$a_{mix}(\omega \to 0) = a_f * \sqrt{\frac{1}{1 + \frac{\varphi_p \rho_p}{\rho_f}}} \cong a_f * \sqrt{\frac{1}{1 + \frac{1}{AFR}}}$$

Figure 9:
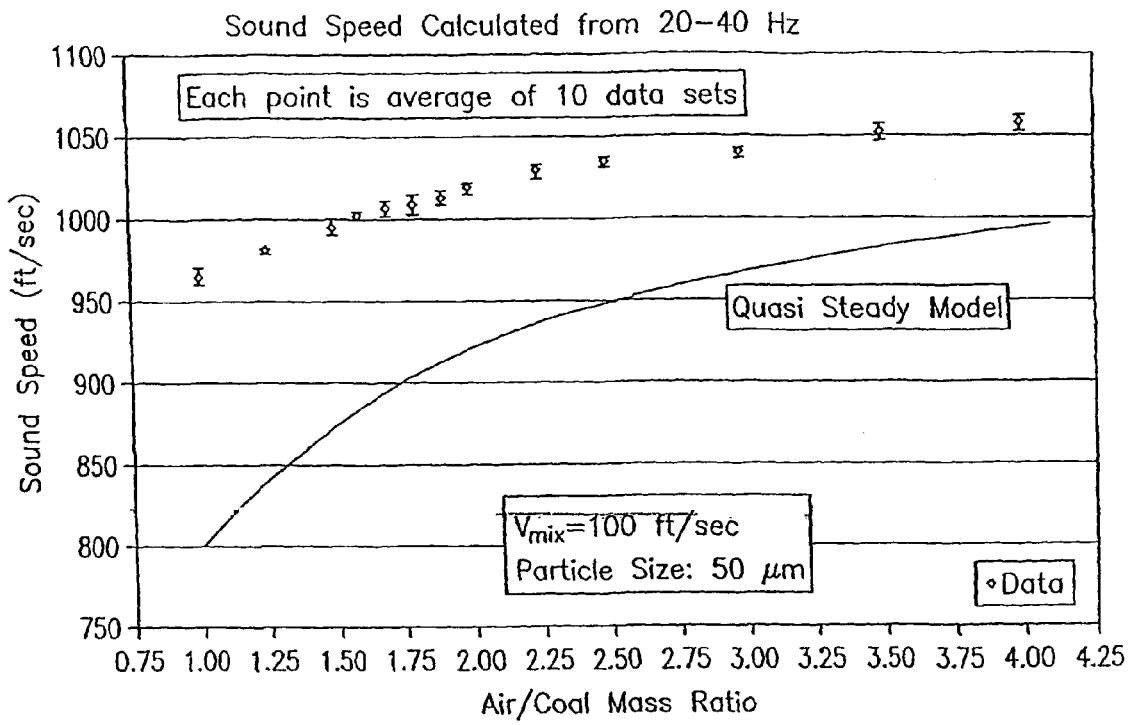
FIG. 9 is a plot of sound speed as function of air/coal ratio in accordance with the present invention.

Note that particle size does not affect the low frequency limit of the sound speed. Referring to FIG. 9, the sound speed was measured using an embodiment of the present invention having eight sensors at 20.5 inch spacing, averaged from 20-40 Hz, for a range of air-to-coal mass ratios. The sound speed predicted for the coal/air mixtures using the quasi-steady model are also presented. As shown, although the general trend is captured, i.e. sound speed decreases with increased coal loading, the error is significant, rendering a first principle interpretation, based on a quasi-steady model inadequate.

In the high frequency limit, the dispersion relation predicts the sound speed with asymptote towards the sound speed of the pure fluid.

$$a_{mix}(\omega ==> \infty) = a_{fluid}$$

Interestingly, the high frequency limit is independent of both particle size and air-to-fuel ratio.

Given the difficulties measuring sufficiently low frequencies to apply the quasi-steady model and recognizing that the high frequency sound speed contains no direct information on either particle size or air-to-fuel ratio, it becomes apparent that the dispersive characteristics of the coal/air mixture should be utilized to determine particle size and air-to-fuel ratio based on speed of sound measurements.

As described hereinbefore, the flow meter 10 of the present invention includes the ability to accurately determine the average particle size of the coal in the PF/air mixture within the pipe 14 and the air to fuel ratio. Provided there is no appreciable slip between the air and the solid coal particle, the propagation of one dimensional sound wave through multiphase mixtures is influenced by the effective mass and the effective compressibility of the mixture. For an air transport system, the degree to which the no-slip assumption applies is a strong function of particle size and frequency. In the limit of small particles and low frequency, the no-slip assumption is valid. As the size of the particles increases and the frequency of the sound waves increase, the non-slip assumption becomes increasing less valid. For a given average coal particle size, the increase in slip with frequency causes dispersion, or, in other words, the sound speed of the mixture to change with frequency. With appropriate calibration the dispersive characteristic of a mixture will provide a measurement of the average particle size, as well as, the air to fuel ratio (particle/fluid ratio) of the mixture.

Using the model described above, which yields the equation shown below, and experimentally determined sound speed as function of frequency, the present invention includes an optimization procedure to simultaneously determine particles size and AFR in coal/air mixtures:

$$a_{mix}(\omega) = a_f \sqrt{\frac{1}{1 + \frac{\varphi_p \rho_p}{\rho_f\left(1 + \omega^2 \frac{\rho_p^2 v_p^2}{K^2}\right)}}}$$

Figure 10:
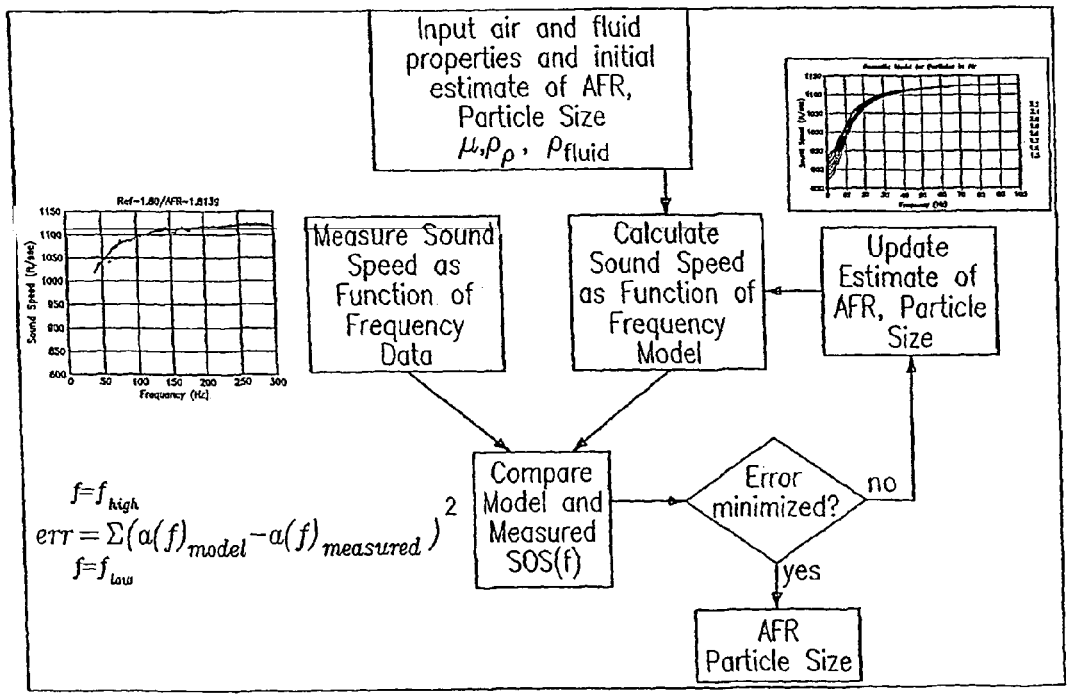
FIG. 10 is a flow diagram of an optimization procedure employed to determine air-to-fuel ratio and particle size from analytical model and experimentally determined dispersive speed of sound data in accordance with the present invention.

Referring to FIG. 10 there is shown an optimization procedure in accordance with the present invention in which the free parameters of an analytical model are optimized to minimize an error function. For illustration purposes, the error function utilized is the sum of the differences of the sound speeds between an analytical model and the experimentally determined sound speed as a function of frequency:

$$err = \sum_{f=f_{low}}^{f=f_{high}} (a(f)_{model} - a(f)_{measured})^2$$

Figure 11:
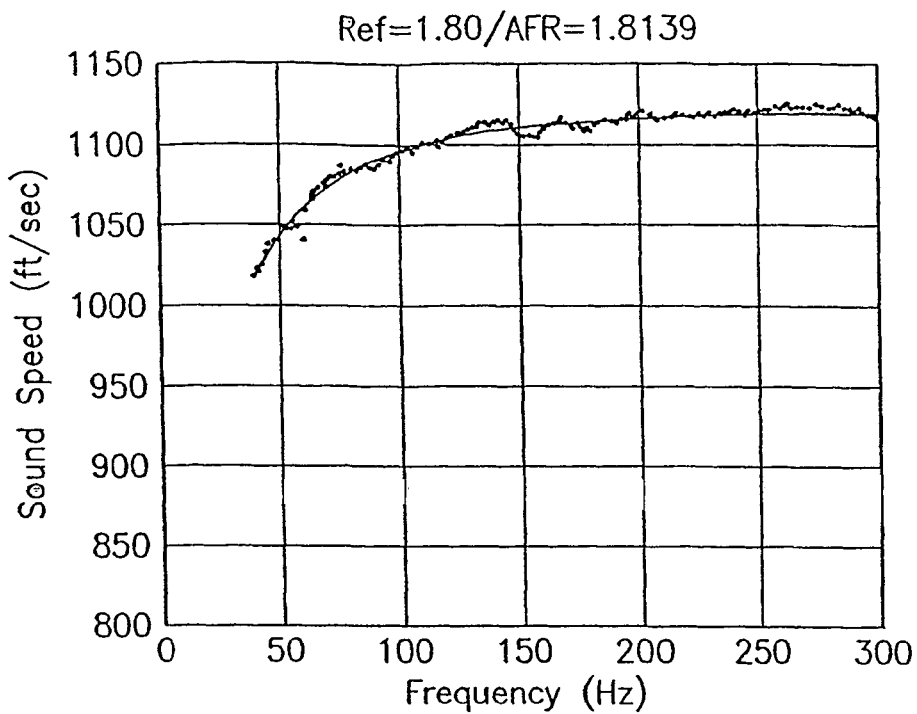
FIG. 11 is a plot of the results of the optimization procedure of FIG. 10 applied to data recorded from an array of sensors listening to flow in a six inch circular duct, 50 μm particle size, 100 ft/sec air flow rate with an air-to-fuel ratio of 1.8.

The results of the optimization procedure applied to data recorded from an array of sensors listening to flow in a six inch circular duct, 50 μm particle size, 100 ft/sec air flow rate with an air-to-fuel ratio of 1.8 is shown in FIG. 11. The measured and optimized-model-predicted sound speed is shown. As shown, the model captures the transitional frequency range well and provides a good estimate of the air-to-fuel ratio.

Figure 12:
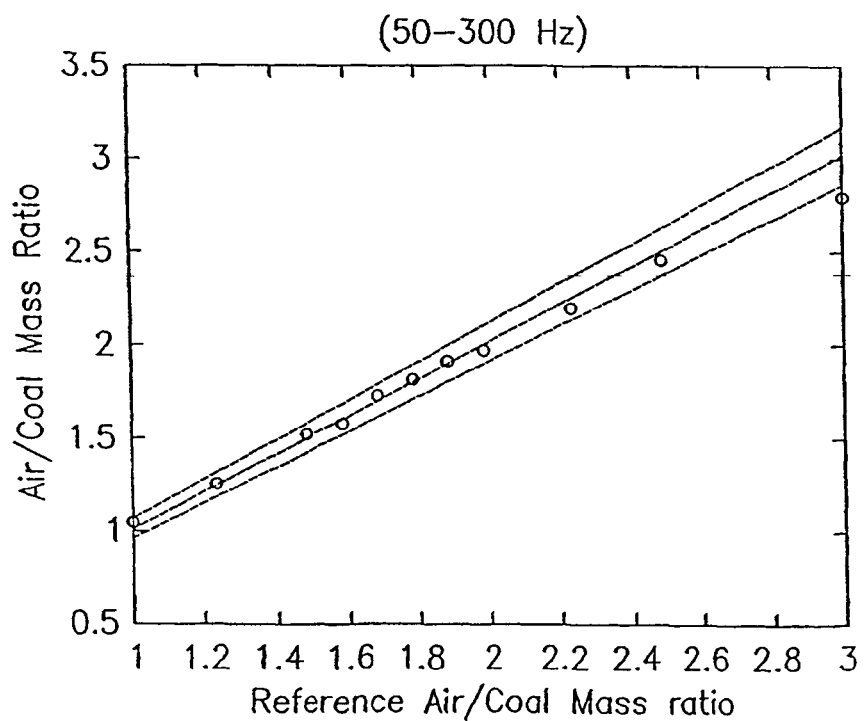
FIG. 12 is a plot of the results of the optimization procedure of FIG. 10 applied to a series of data sets with varying air-to-fuel ratio.

The results of the optimization procedure applied to a series of data sets with varying air-to-fuel ratio is shown in FIG. 12. Note for this optimization the particle size was held constant over the range of data sets.

As suggested herein before, the length of the array of pressure sensors should be at least a significant fraction of a wavelength of the sound speed of interest. The significant fraction of the wavelength may be at least thirty percent of the wavelength, however, this fraction may be less than thirty percent depending on the desired accuracy of the measurement, the measured wavelength and/or the strength of the acoustic wave (e.g., low signal/noise ratio). Therefore, the length of the array is dependent on the frequency of the sound speed of interest (frequency being inversely proportional to wavelength), wherein the frequency of the sound speed of interest is dependent on the measurement to be determined (e.g., air/particle ratio and particle size) and the dispersion characteristics of the mixture. For example, the low frequency range of the plot of the speed of sound (quasi-steady state) for measuring the concentration of the mixture (e.g., air/particle ratio), shown in FIG. 7, is lower as dispersion of the mixture increases. As described herein before, the dispersion characteristics of the mixture is dependent on the size of the particles among other factors. As the particle size increases, the dispersion becomes greater, and as the particle size decreases, the dispersion becomes lower. Consequently, the length of the array is a function of the size of the particle within the mixture, and therefore, as best shown in FIG. 8, the transition point (low frequency cut-off) between the low frequency range and the intermediate frequency decreases in frequency as the particle size increases.

For example when measuring the concentration of the mixture, as the size of the particles increase, the low frequency cut-off decreases and thus, the acoustic wavelength of interest increases to thereby necessitate the length of the array to be longer. Conversely, as the size of the particles decrease, the low frequency cut-off increase and thus, the acoustic wavelength of interest decreases to thereby necessitate the length of the array to be shorter. Simply stated, the larger the particle, the longer the array and vice versa. The same comparison is true when determining the size of the particles within the mixture. However, for optimal performance of the flow meter, the measurement of the concentration of the mixture may require a longer array than the measurement of the particle size because measurement of the concentration is at a lower frequency (longer wavelength) than the intermediate frequency (shorter wavelength) of the particle size.

The lowest practical measurable frequency range is approximately 10-25 Hz, therefore the measurement of large particle may not be possible to measure the quasi-steady model, which may in some instances be less than 10 Hz (i.e., cut-off frequency less than 10 Hz). Under these circumstances, the frequency of the speed of sound of interest is above the cut-off frequency. However, the measured speed of sound is curve fit to a dispersion model of the mixture by varying the size of the particle and the composition of the mixture to determine the particle size and/or concentration of the mixture, as shown in FIG. 10 that will be described in greater detail hereinafter.

While the length of the array is dependent on the particle size, the length may also be dependent on other parameters that define the amount of dispersion, such as mass of the particles and the viscosity of the fluid within the mixture.

Another factor that defines (or effects) the length of the array of pressure sensors 15-18 includes the signal strength of the acoustic wave received by the processor. As the signal strength improves or is greater, the shorter the length of the array must be. The signal strength is dependent on a number of factors, such as the strength of the acoustic wave itself, the signal/noise ratio of the sensors, the matching of the sensors and others.

The spacing may be equi-spaced as shown in FIG. 1, however the flow meter 10 of the present invention contemplates that the sensors may have non-equal or uneven spacing therebetween. The sensors may be spaced any desired distance, provided the location or position of the sensors are known. For ported pressure sensors, the minimum spacing is limited by mechanical limitations of the sensors. For strain-based sensors, such as PVDF bands described hereinafter, the compliance of the pipe limits the closeness of the spacings. For example, the more rigid the pipe, the greater the spacing of the sensors must be, and conversely, the more compliant the pipe, the closer the sensors may be spaced.

The spacing of the pressure sensors may also be defined by the number of sensors disposed within an array of a given length. The more sensors disposed within the array of a given length, the closer the spacing. The number of sensors disposed within an array is dependent on the required or desired accuracy of the flow meter 10. The greater the number of sensors in the array, a more precise measurement of the acoustic pressure field can be achieved. In other words, a greater number of samples or measurements of the acoustic pressure wave over a given length of the array (or wavelength) provided the sensors enable greater resolution in the measurement of the acoustic wave to be measured or characterized.

In addition to measuring the fluid to particle ratio of the mixture 12 and particle size within a pipe 14 using the measured speed of sound, the flow meter 10 further includes the ability to measure of volumetric flow rate of the mixture by comparing the difference of the speed of one dimensional sound waves propagating with and against the mean flow.

This method of determining the volumetric flow rate of the particle/fluid mixture 12 within pipe 14 relies on the interaction of the mean flow with the acoustic pressure field. The interaction results in sound waves propagating with the mean flow traveling at the speed of sound (if the particle/liquid mixture were not flowing) plus the convection velocity and, conversely, sound waves traveling against the mean flow propagating at the speed of sound minus the convection velocity. That is, $$a_R = a_{mix} + u$$

$$a_L = a_{mix} - u$$

where $a_R$=velocity of a right traveling acoustic wave relative to a stationary observer (i.e. the pipe 14), $a_L$=velocity of a left traveling acoustic wave apparent to a stationary observer, $a_{mix}$=fluid speed of sound (if the fluid were not flowing) and u=the mean flow velocity (assumed to be flowing from left to right in this instance). Combining these two equations yields an equation for the mean velocity, $$u = \frac{a_R - a_L}{2}$$

Therefore, by measuring the propagation velocity of acoustic waves in both directions relative to the stationary pipe as described hereinbefore, the mean flow velocity can be calculated by multiplying the mean flow velocity by the cross-sectional area of the pipe 14.

The practicality of using this method to detemilne the mean flow is predicated on the ability to resolve the sound speed in both directions with sufficient accuracy to determine the volumetric flow. For typical liquid measurements, flow velocities are typically at ~10 ft/sec and sound speeds of ~4000 ft/sec. Thus axial mach numbers are on the order of 10/4000 of 0.0025. For a +/−10% accuracy in flow rate (+/−7ft/sec), the sound speed of the upstream and downstream propagating waves would need to be resolved to +/−0.5/4000 or one part in 8,000.

However, for PF/air mixture flows, axial flow velocities are nominally around 70 ft/sec with no flow sound speeds of ~700 ft/sec. This results in mach numbers of ~0.1, approximately two orders of magnitude greater than typical liquid flows For pulverized fuel flows, to resolve the flow rate to 10% accuracy (or +/−7 ft/sec), one would have to resolve the sound speed to +/−3.5 ft/sec. or 3.5/700 or one part in 200.

For the sound speed measurement, the flow meter 10 utilizes similar processing algorithms as those employed herein before. The temporal and spatial frequency content of sound propagating within the process piping 14 is related through a dispersion relationship.

$$\omega = k a_{mix}$$

The wave number is k, which is defined as k=2π/λ, ω is the temporal frequency in rad/sec, and $a_{mix}$ is the speed at which sound propagates within the process piping. For this cases where sound propagates in both directions, the acoustic power is located along two acoustic ridges, one for the sound traveling with the flow at a speed of $a_{mix} + V_{mix}$ and one for the sound traveling against the flow at a speed of $a_{mix} - V_{mix}$.

Figure 13:
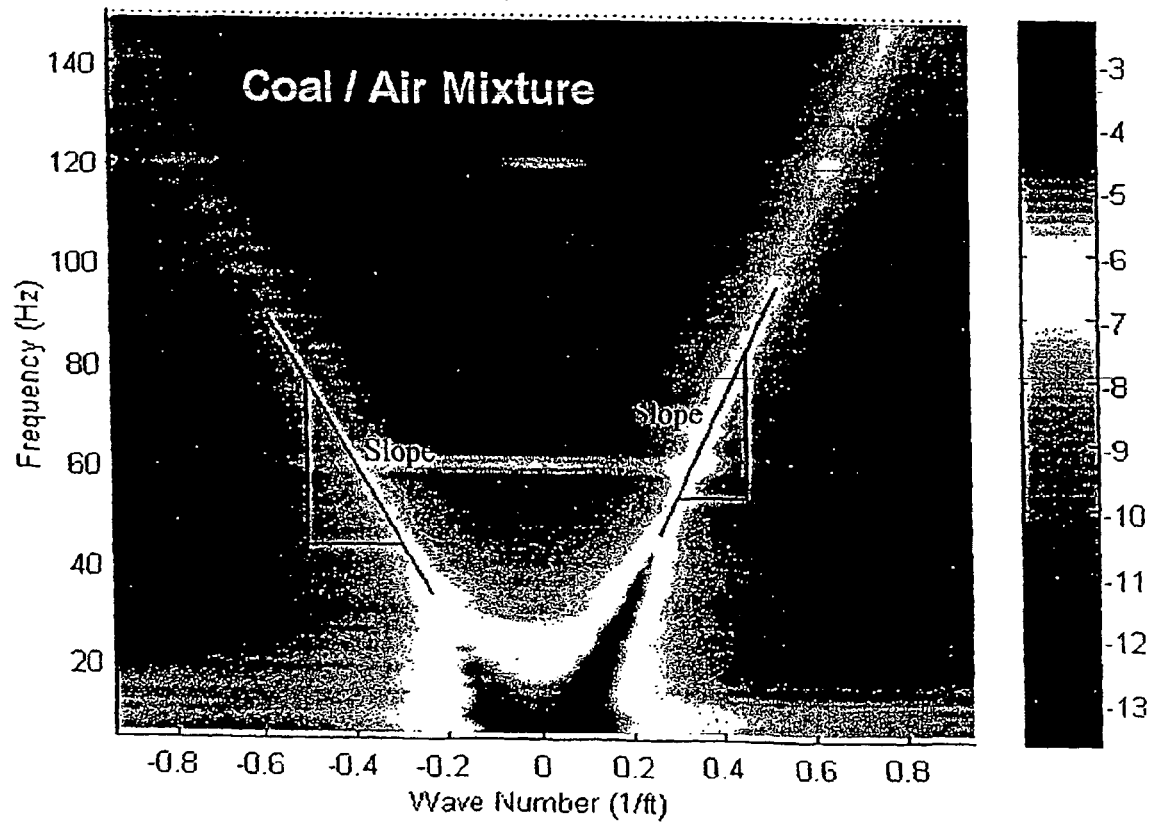
FIG. 13 is a kω plot of data processed from an array of pressure sensors use to measure the speed of sound of a coal/air mixture flowing in a pipe, in accordance with the present invention.

The k-w plot shown in FIG. 13 illustrates the fundamental principle behind sonar based flow measure, namely that axial arrays of pressure sensors can be used in conjunction with sonar processing techniques to determine the speed at which naturally occurring turbulent eddies convect within a pipe. FIG. 13 shows a k-ω plot generated for acoustic sound field of a coal/air mixture flowing through a pipe. Two acoustic ridges are clearly evident. Each of the slopes of the two depicted acoustic ridges respectively defines the speed of sound traveling with and against the mean flow, respectively. A parametric optimization method was used to determine the "best" line representing the slope of the acoustic ridge.

Further, FIG. 13 illustrates the ability of the present invention to determine the velocity of a fluid moving in a pipe. FIG. 13 shows a wavenumber-frequeney plot (k-w plot) of unsteady pressure. The contours represent the relative signal power at all combinations of frequency and wavenumber. The highest power "ridges" represent the acoustic wave with slope of the ridges equal to the propagation speed. The dashed lines show the best-fit two-variable maximization of the power with the two variables being sound speed and flow velocity. The right-side ridge represents the acoustic wave traveling in the same direction as the bulk flow and therefore its slope is steeper than the left-side ridge that represents the acoustic wave traveling in the opposite direction of the bulk flow. This indicates that the acoustic wave traveling in the same direction of the flow is traveling faster than the acoustic wave traveling in the opposite direction of the bulk flow relative to the stationary sensors located on the pipe.

The pressure sensors 15-18 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 15-18 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702. Alternatively, the sensors 14 may be electrical or optical strain gages attached to or embedded in the outer or inner wall of the pipe which measure pipe wall strain, including microphones, hydrophones, or any other sensor capable of measuring the unsteady pressures within the pipe 14. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

For any of the embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe 14. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe 14 if desired.

It is also within the scope of the present invention that any other strain sensing technique may be used to measure the variations in strain in the pipe, such as highly sensitive piezoelectric, electronic or electric, strain gages attached to or embedded in the pipe 14.

In certain embodiments of the present invention, a piezoelectronic pressure transducer may be used as one or more of the pressure sensors 15-18 and it may measure the unsteady (or dynamic or ac) pressure variations inside the pipe 14 by measuring the pressure levels inside of the pipe. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

Figure 14:
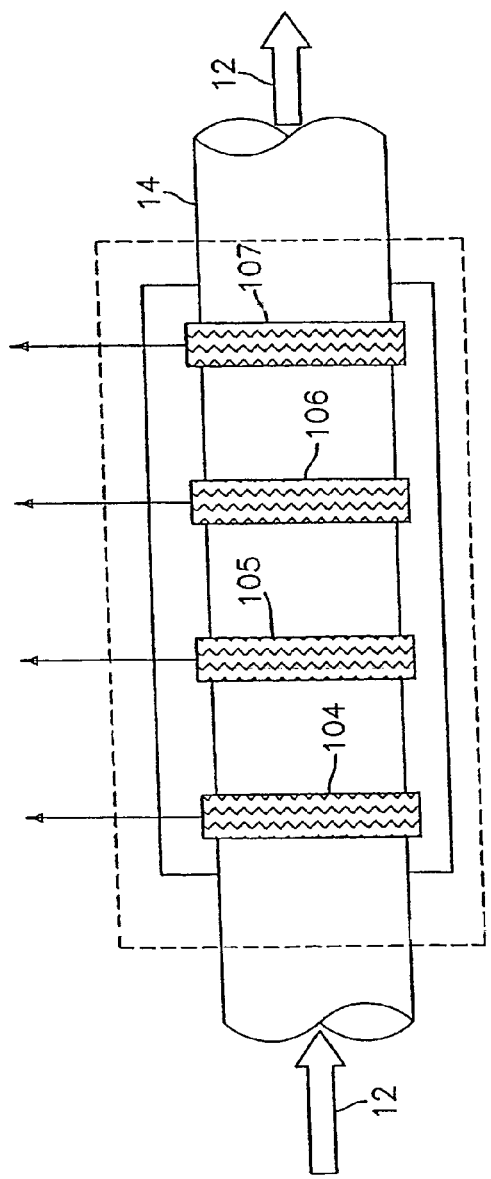
FIG. 14 is a side elevational view of a plurality of pressure sensors, having PVDF, clamped to the outer surface of the pipe, in accordance with the present invention.

Furthermore the present invention contemplates tat each of the pressure sensors 15-18 of the flow meters 10,70 may include a piezoelectric sensor 104-107 that provides a piezoelectric material 110 to measure the unsteady pressures of the fluid/particle mixture 12 as shown in FIG. 14. The piezoelectric material, such as the polymer, polarized fluoropolymer, polyvinylidene fluoride (PVDF), measures the strain induced within the process pipe 14 due to unsteady pressure variations within the process mixture 12. Strain within the pipe is transduced to an output voltage or current by the attached piezoelectric sensors 104-107.

Figure 15:
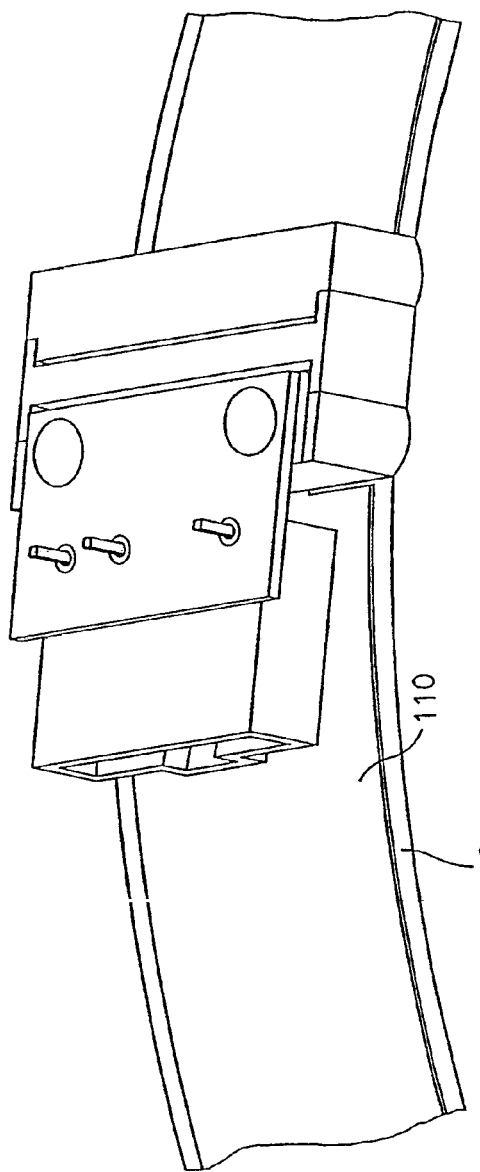
FIG. 15 is a partial perspective view of one of the pressure sensors of FIG. 14.

As best shown in FIG. 15, the PVDF material 110 is adhered to the outer surface of a steel strap 112 that extends around and clamps onto the outer surface of the pipe 14. The piezoelectric sensing element is typically confonnal to allow complete or nearly complete circumferential measurement of induced strain to provide a circumference-averaged pressure. The sensors can be formed from PVDP films, co-polymer films, or flexible PZT sensors, similar to that described in "Piezo Film Sensors technical Manual" provided by Measurement Specialties, Inc., which is incorporated herein by reference. The advantages of this technique are the following:

1. Non-intrusive flow rate measurements
2. Low cost
3. Measurement technique requires no excitation source. Ambient flow noise is used as a source.
4. Flexible piezoelectric sensors can be mounted in a variety of configurations to enhance signal detection schemes. These configurations include a) co-located sensors, b) segmented sensors with opposing polarity configurations, c) wide sensors to enhance acoustic signal detection and minimize vortical noise detection, d) tailored sensor geometries to minimize sensitivity to pipe modes, e) differencing of sensors to eliminate acoustic noise from vortical signals.
5. Higher Temperatures (140C.) (co-polymers)

While the present invention illustrates that the array of pressure sensors comprises a plurality of like sensors, the present invention contemplates that any combination of different or similar pressure sensors may be used within an array.

While the present invention is capable of measuring solid particles suspended in a fluid, one will appreciate that other multi-phase mixtures or flows may be measured using an array of sensors, such as steam flow. It is further recognize the that effects of dispersion on large solid particles in a fluid would be similar to large droplets of a liquid dispersed in a gas or air, and thus similar considerations when measuring the steam quality and droplet size should be addressed.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring at least one parameter of a dispersive mixture of solids and fluid flowing in a pipe, said apparatus comprising:

a spatial array of pressure sensors, disposed at different axial locations along the pipe, to measure an pressure within the pipe at each corresponding axial location, each of said sensors providing a pressure signal indicative of the pressure within the pipe at said corresponding axial location; and a signal processor, responsive to said pressure signals, to determine the speed of sound propagating through the dispersive mixture as a function of frequency at multiple frequencies and to use the speed of sound and a dispersion model of the dispersive mixture to provide output corresponding to at least one parameter of the dispersive mixture flowing in the pipe.

2. The apparatus of claim 1, wherein each sensor measures an acoustic pressure and provides a signal indicative of an acoustic noise within the pipe.

3. The apparatus of claim 1, wherein the signal processor, responsive to said pressure signals, outputs the speed of sound propagating through the mixture in the pipe.

4. The apparatus of claim 3, wherein said signal processor comprises logic which calculates a speed at which sound propagates axially past said spatial array.

5. The apparatus of claim 4, wherein said pressure signals each comprise a frequency based signal and wherein said signal processor comprises logic which calculates a ratio of two of said frequency based signals.

6. The apparatus of claim 3, wherein said signal processor comprises logic which calculates a frequency based signal for each of said pressure signals.

7. The apparatus of claim 3, wherein the signal processor comprises logic which calculates a fluid composition of the mixture in the pipe.

8. The apparatus of claim 3, wherein the array of pressure sensors are spaced sufficiently such that the entire length of the array is at least a significant fraction of a measured wavelength of acoustic waves being measured.

9. The apparatus of claim 1, comprising at least three of said sensors.

10. The apparatus of claim 1, wherein at least one of said pressure sensors measures a circumferential pressure at said axial location of said sensor.

11. The apparatus of claim 10 wherein at least one of said pressure sensors includes a piezoelectric film material.

12. The apparatus of claim 11, wherein the piezoelectric film material is polarized fluoropolymer, polyvinylidene fluoride (PVDF).

13. The apparatus of claim 1, wherein each of said pressure sensors is a strain sensor that measures strain on the pipe.

14. The apparatus of claim 1, wherein the signal processor uses the speed of sound propagating through the mixture to characterize dispersion properties of the mixture and compares the dispersion properties of the mixture to a dispersion model of the mixture to provide a signal indicative of the at least one parameter of the mixture.

15. The apparatus of claim 1, wherein the dispersion model is empirically derived.

16. The apparatus of claim 1, wherein the dispersion model is numerically derived.

17. The apparatus of claim 16, wherein the numerically derived dispersion model is:

$$a_{mix}(\omega) = a_f \sqrt{\cfrac{1}{1 + \cfrac{\varphi_p \rho_p}{\rho_f \left(1 + \omega^2 \cfrac{\rho_p^2 v_p^2}{K^2}\right)}}}$$

wherein $\alpha_{mix}(\omega)$=speed of sound propagating through the mixture; $\alpha_f$=speed of sound propagating through the fluid; $\phi_p$=volume fraction of the particles; $\omega$=frequency; $\rho_p,\rho_f$=density of particles and fluid, respectively; $\upsilon$=volume of a particle; K=proportionality constant.

18. The apparatus of claim 1, wherein the at least one parameter of the mixture includes at least one of a particle/fluid composition, a volumetric phase fraction, a volumetric flow rate, particle size, mass flow, density, velocity of the mixture in the pipe, and a speed of sound propagating through the mixture in the pipe.

19. The apparatus of claim 1, wherein the signal processor further characterizes the dispersion properties of the mixture in response to at least one of the pressure of the mixture, temperature of the mixture, density of particle phase and density of the fluid phase.

20. The apparatus of claim 1, wherein the signal processor compares at least a transitional frequency range of the dispersion model to determine an average particle size in the mixture.

21. The apparatus of claim 1, wherein the signal processor compares at least one of a lower frequency range and a transitional frequency range of the dispersion model to determine a particle/fluid ratio of the mixture.

22. The apparatus of claim 1, wherein the signal processor defines an acoustic ridge in a k-$\omega$ plane and determines a slope of the at least a portion of the acoustic ridge to determine the speed of sound propagating through the mixture.

23. The apparatus of claim 1, wherein the sensors include at least one of pressure sensors and strain-based sensors.

24. The apparatus of claim 1, wherein the unsteady pressure is a passive acoustic wave propagating axially through the dispersive mixture flowing in the pipe.

25. The apparatus of claim 1, wherein the spatial array includes at least two pressure sensors.

26. A method for measuring at least one parameter of a dispersive mixture of a solid and fluid flowing in a pipe, said method comprising:

measuring pressures within the pipe at at least two axial measurement locations disposed along the pipe to provide corresponding pressure signals indicative of the pressure within the pipe at each of the at least two axial measurement locations;

determining the at least one parameter of the dispersive mixture of a solid and fluid flowing in the pipe using the pressure measured at the axial measurement locations to determine the speed of sound propagating through the mixture as a function at multiple frequencies and using the speed of sound and a dispersion model of the dispersive mixture, and generating an output corresponding to the at least one parameter.

27. The method of claim 26, wherein the measured pressures are acoustic pressures to provide a signal indicative of an acoustic noise within the pipe.

28. The method of claim 27, wherein the determining the at least one parameter uses an acoustic pressure to calculate a speed of sound propagating in the pipe.

29. The method of claim 28, wherein a spatial array of sensors measures said pressure and the determining the at least one parameter uses an acoustic pressure to calculate a speed at which sound propagates axially past said spatial array.

30. The method of claim 29, wherein said acoustic pressure signals each comprise a frequency based signal and wherein said method further includes providing a signal processor comprising logic which calculates a ratio of two of said frequency based signals.

31. The method of claim 28, wherein the determining the at least one parameter uses an acoustic pressure to calculate a frequency based signal for each of said acoustic pressure signals.

32. The method of claim 28, wherein the step of determining the at least one parameter uses an acoustic pressure to calculate a fluid composition of the mixture in the pipe.

33. The method of claim 28, further including providing an array of pressure sensors, and said step of measuring pressures includes measuring acoustic waves, said array of pressure sensors being spaced sufficiently such that an entire length of the array is at least a significant fraction of a measured wavelength of the acoustic waves being measured.

34. The method of claim 26, further comprising providing at least three sensors to measure the unsteady pressure.

35. The method of claim 26, wherein measuring pressure includes measuring a circumferential pressure at at least an axial location of a sensor.

36. The method of claim 35, wherein said sensor includes a piezoelectric film material.

37. The method of claim 36, wherein the piezoeleetric film material is polarized fluorop.olymer, polyvinylidene fluoride (PVDF).

38. The method of claim 26, wherein the step of measuring pressures includes providing at least one strain sensor that measures strain on the pipe to provide at least a portion of the corresponding pressure signals.

39. The method of claim 26, wherein said determining the at least one parameter uses the speed of sound propagating through the mixture to characterize dispersion properties of the mixture and compares the dispersion properties of the mixture to a dispersion model of the mixture to provide a signal indicative of the at least one parameter of the mixture.

40. The method of claim 26, wherein the dispersion model is empirically derived.

41. The method of claim 26, wherein the dispersion model is numerically derived.

42. The method of claim 41, wherein the numerically derived dispersion model is:

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

wherein $\alpha_{mix}(\omega)$=speed of sound propagating through the mixture; $\alpha_f$=speed of sound propagating through the fluid; $\phi_p$=volume fraction of the particles; $\omega$=frequency; $\rho_p, \rho_f$=density of particks and fluid, respectively; $\upsilon$=volume of a particle; K=proportionality constant.

43. The method of claim 26, wherein said solids are particulate and the at least one paramcter of the mixture includes at least one of a particle/fluid composition, a volumetric phase fraction, a volumetric flow rate, particle size, mass flow, density, velocity of the mixture in the pipe, and speed of sound propagating through the mixture in thc pipe.

44. The method of claim 26, wherein said step of determining the at least one parameter further characterizes the dispersion properties of the mixture in response to at least one of the pressure of the mixture, temperature of the mixture, density of particle phase and density of the fluid phase.

45. The method of claim 26, wherein said step of determining the at least one parameter compares at least an intermediate frequency range of the dispersion model to determine the average particle size in the mixture.

46. The method of claim 26, wherein said calculating the at least one parameter compares at least one of a lower frequency range and an intermediate frequency range of the dispersion model to determine a particle/fluid ratio of the mixture.

47. The method of claim 26, further includes determining a frequency based signal for each of said pressure signals.

48. The method of claim 26, wherein the measuring of unsteady pressures within the pipe is accomplished using at at least one of 3, 4, 5, 6, 7, 8, 9, 10, 11, 12, 13, 14, 15 and 16 sensors disposed at respective axial locations.

49. The method of claim 26, wherein said step of determining the at least one parameter defines an acoustic ridge in a k-$\omega$plane and determines a slope of at least a portion of a acoustic ridge to determine the speed of sound propagating through the mixture.

50. An apparatus for measuring at least one parameter of a dispersive mixture of a solid and a fluid flowing in a pipe, said apparatus comprising:
    a signal processor, responsive to a signal indicative of the speed of sound propagating through the dispersive mixture of a solid and a fluid flowing within the pipe as a function of frequency at multiple frequencies, to determine the at least one parameter of the dispersive mixture in the pipc using a dispersion model of the dispersive mixture, said signal processor being configured to produce an output corresponding to the at least one parameter.

51. The apparatus of claim 50, wherein the signal processor further characterizes the dispersion properties of the dispersive mixture and compares the dispersion properties of the mixture to a dispersion model of thc dispersive mixture to provide a signal indicative of the at least one parameter of the mixture.

52. A method for measuring at least one parameter of a dispersive mixture of a solid and a fluid flowing in a pipe, said method comprising:
    receiving a signal indicative of the speed of sound propagating through the dispersive mixture of a solid and a fluid flowing in a pipe as a function of frequency at multiple frequencies;
    determining the at least one parameter of the dispersive mixture in the pipe using the signal indicative of the speed of sound at multiple frequencies and a dispersion model of the dispersive mixture; and
    producing an output corresponding to the at least one parameter.

53. The method of claim 52, wherein said determining the at least one parameter furthet characterizes dispersion properties of the mixture using the signal indicative of the speed of sound propagating through the mixture and compares the dispersion properties of the mixture to a dispersion model of the mixture to provide a signal indicative of the at least one parameter of the mixture.

* * * * *